(12) United States Patent
Fischer et al.

(10) Patent No.: US 8,012,413 B2
(45) Date of Patent: Sep. 6, 2011

(54) GASEOUS STERILIZATION OF IMPERMEABLE CONTAINERS THROUGH USE OF POROUS MATERIAL

(75) Inventors: Eric Fischer, Freehold, NJ (US); Gary Mitchel, Belle Mead, NJ (US); Michael J O'Neil, West Barnstable, MA (US)

(73) Assignee: DePuy Spine, Inc., Raynham, MA (US)

( * ) Notice: Subject to any disclaimer, the term of this patent is extended or adjusted under 35 U.S.C. 154(b) by 717 days.

(21) Appl. No.: 11/614,967

(22) Filed: Dec. 21, 2006

(65) Prior Publication Data

US 2008/0152536 A1   Jun. 26, 2008

(51) Int. Cl.
*A61L 2/20* (2006.01)
*A61M 5/32* (2006.01)

(52) U.S. Cl. .......................................... 422/28; 604/199
(58) Field of Classification Search .................. None
See application file for complete search history.

(56) References Cited

U.S. PATENT DOCUMENTS

| | | |
|---|---|---|
| 4,340,067 A | 7/1982 | Rattenborg |
| 5,870,885 A | 2/1999 | Biddle |
| 5,955,296 A | 9/1999 | Roll |
| 5,989,852 A | 11/1999 | Hendricks |
| 5,997,544 A | 12/1999 | Nies |
| 6,186,960 B1 | 2/2001 | Tripp |
| 7,252,856 B2 | 8/2007 | Cohen |
| 7,381,201 B2 | 6/2008 | Gilbert |
| 2005/0092685 A1 | 5/2005 | Hilhorst |
| 2005/0135963 A1 | 6/2005 | Rodriguez |

OTHER PUBLICATIONS

International Search Report dated Jun. 9, 2008 for PCT/US07/88325.

*Primary Examiner* — Walter D Griffin
*Assistant Examiner* — Timothy Cleveland
(74) *Attorney, Agent, or Firm* — Thomas M. Di Mauro (57) ABSTRACT

A gas-impervious container having a gas-permeable porous insert, wherein the insert contacts a flowable biomedical material, for improving access of the sterilant gas to the material.

2 Claims, 6 Drawing Sheets

GASEOUS STERILIZATION OF IMPERMEABLE CONTAINERS THROUGH USE OF POROUS MATERIAL

BACKGROUND OF THE INVENTION

One requirement of a biomedical implant material is that it must be capable of being sterilized. Since many implant materials are flowable, they must be housed in a container. However, sterilizing the flowable implant material independently from the container, and then aseptically assembling the two units increases the risk of contamination and bioburden. Therefore, sterilization efforts have focused upon sterilizing the flowable implant material while it is housed in the container.

However, it is often the case that such prefilled containers can not be sterilized by traditional approaches (such as irradiation or heat) because the biomedical implant material contained within the container does not remain in a stable condition when undergoing these processes.

As a result of these shortcomings, a gaseous disinfectant is often used in implant-container sterilization procedures. For example, in one such approach, a biomedical implant material is housed in a syringe, and gas is allowed to permeate the material through the two open ends of the syringe. However, due to the slow rate of gas permeation through the implant material, implant material sterilization using this approach can not be accomplished in a practical time frame.

It has been suggested that vents be applied at both ends of the syringe, as this approach has been successfully used to sterilize the internal surfaces of an empty syringe. However, when this approach was tried with a syringe having a curable silicone composition therein, complete sterilization of the composition was not achieved even after 18 hours with high sterilent gas concentrations.

Deep vacuum processes have also been considered to facilitate delivery of sterilent gas into empty syringes. However, such processes offer no advantage when attempting to sterilize a filled syringe.

U.S. Pat. No. 5,997,544 (Nies) discloses a process for making bone cement, utilizing a sterile filter to allow gas entry and release.

U.S. Pat. No. 5,989,852 (Hendricks) discloses the insertion and positioning of a compressible insert to regulate the amount of gas entering a chamber as a test indicator of the amount of sterilant penetration. It does not disclose the use of an insert that protrudes into the material, nor a cartridge insert providing sterilant penetration.

U.S. Pat. No. 5,870,855 (Biddle) discloses the insertion and positioning of a gas-transmissive plug positioned to regulate the amount of gas entering a chamber as a test indicator of the amount of sterilant penetration. It does not disclose the use of an insert that protrudes into the material, nor a cartridge insert providing for sterilant penetration.

SUMMARY OF THE INVENTION

It is an object of the present invention to provide a means to terminally sterilize a flowable implant material (and particularly one that is neither heat—nor radiation-stable) after it has been packaged in a sealed syringe.

The present invention provides a porous sleeve that fits within the syringe (or any other container adapted to hold a biomedical implant material) and fluidly communicates with the atmosphere outside the syringe. Placement of the porous sleeve adjacent or within the implant material creates a path of least resistance for the permeation of gas located at an open end of the container and effectively decreases the maximum gas permeation length through the material packaged in the container. This enables the material to be sterilized by a gaseous agent while it is in the container within a practical time frame.

Therefore, there is provided a process and device for producing a sterilized material housed in a container, wherein the material is sterilized while it is housed in the container. In some embodiments, the present invention relates to a gas-impervious container (such as a syringe) having a barrel, and a porous sleeve inserted into the barrel.

Therefore, in accordance with the present invention, there is provided a gas-impervious container having a biomedical material therein and a gas-permeable porous insert having a first end, wherein the insert contacts the flowable biomedical material.

Also in accordance with the present invention, there is provided a method of sterilizing a biomedical material, comprising the steps of:
a) providing a gas-impervious container having an open end and flowable biomedical material therein and a gas-permeable porous insert, and
b) exposing the open end of the container to a gaseous sterilant).

Also in accordance with the present invention, there is provided a kit comprising:
a) a cartridge having a first bore defining a longitudinal axis, a distal end having a distal endwall, distal openings and activation means, and a proximal end having a proximal opening, and
b) an insert comprising:
i) a gas-permeable, liquid impermeable container having an outer wall, a closed distal end, and a proximal end defining a bore,
ii) a first flowable biomedical material contained within the upper bore of the container.

Also in accordance with the present invention, there is provided a kit comprising:
a) a cartridge having a first bore defining a longitudinal axis, a distal end having a distal endwall, distal openings and activation means, and a proximal end having a proximal opening, and
b) a container having an open end, a flowable biomedical material therein and a gas-permeable porous insert having a first end, wherein the insert contacts the flowable biomedical material.

DETAILED DESCRIPTION OF THE INVENTION

Any biomedical implant material that can be used in biomedical procedures can be sterilized in accordance with the present invention. The procedure of the present invention is advantageously carried out upon a material that is neither heat- nor radiation-stable. In some embodiments, the biomedical implant material is selected from the group consisting of polymers, biologics and drugs that are susceptible to breakdown, cure or change upon infrared radiation, e-beam radiation or heat sterilization.

In one embodiment, the biomedical implant material is a curable silicone material, and in one particular embodiment thereof is Sinux Nucleus Replacement Material, available from Sinitec, located in Zurich, Switzerland.

In many embodiments, the container of the present invention has a substantially elongated shape. Typically, the container has a cylindrical portion and is open at both ends. In some embodiments, the container is a syringe. In some embodiments, the container is a cartridge.

Any porous material that is compatible with the biomedical implant material can be used in accordance with the present invention. In some embodiments, the porous material is a polymer, and preferably is selected from the group consisting of high density polyethylene, polypropylene, tetrafluoroethylene, polyurethane and cellulose. In some embodiments, the porous material is a metal, and preferably is selected from the group consisting of cobalt chrome, titanium, and stainless steel. In some embodiments, the porous material is a ceramic, and preferably is selected from the group consisting of silica glass (including sintered glass) and alumina. In some embodiments, the porous material is a laminate of a porous portion and a dense portion. In some embodiments, the porous material is POREX™, a porous high density polyethylene available from Porex Technologies, Fairburn, Ga.

Preferably, the morphology of the porous material is that of an open cell matrix that allows penetration of the gaseous sterilant (such as ethylene oxide). However, in other embodiments, there is a mixture of open cell and closed cell matrices, wherein the mixture allows for a reduction in the wall thickness of the porous insert while maintaining a burst strength that is adequate for dispensing the implant material.

In conducting some experiments with the device of the present invention, it would discovered that the flowable biomedical material tended to weep through the porous sleeve. The present inventors then developed improvements that address the weeping issue. Therefore, in a first embodiment, the device further includes a thin annular layer of a reduced porosity barrier material that is placed adjacent the porous sleeve, either on the inside or outside of the sleeve. Preferably, this thin layer is made of the same chemical composition as the porous sleeve and is fused to the porous sleeve. Thus, there is provided a porous barrier material having a porosity that is less than that of the porous insert, wherein the porous barrier material is placed adjacent the porous sleeve.

In a second embodiment, a porous coating is provided upon the porous sleeve, either on the inside or outside of the sleeve. These can be spray or dip-applied coatings, including polymers and adhesives such as epoxy, urethane, silicone or cyanoacrylate-based materials. In a third embodiment, process treatments are added to reduce the porosity of the sleeve. These include thermal treatments, mechanical (hot pressing) treatments, ultrasonic pressing and spin welding.

Figure 1:
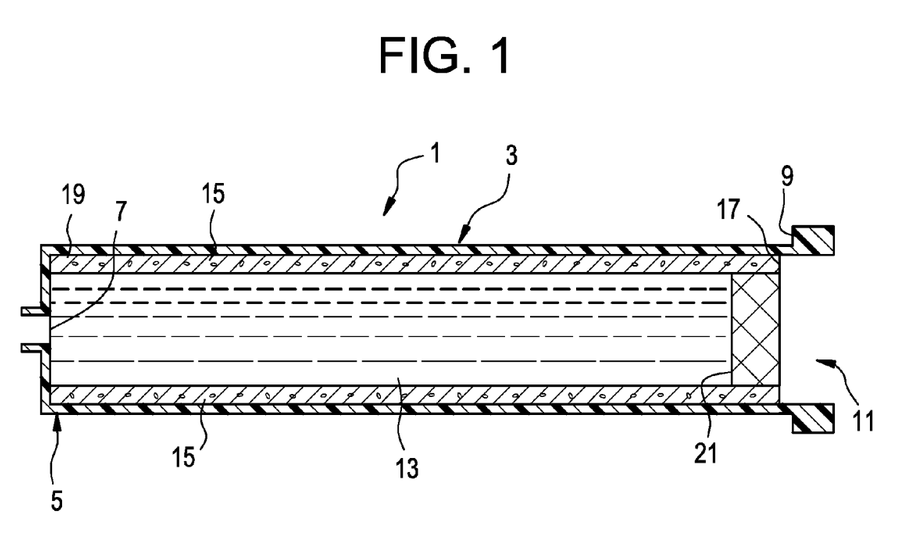
FIG. 1 is a longitudinal cross-section of a single bore embodiment of the present invention having a porous sleeve.

Now referring to FIG. 1, in a first embodiment of the present invention, there is provided a medical device 1 comprising:
   a) a gas-impervious container 3 having a bore defining a longitudinal axis, a distal end 5 having a distal opening 7, and a proximal end 9 having a proximal opening 11,
   b) a flowable biomedical material 13 contained within the bore of the container, and
   c) a gas-permeable porous sleeve 15 contained within the bore of the container and longitudinally disposed along the longitudinal axis of the container, the sleeve having a first end 17 and a second end 19,
wherein the sleeve contacts the flowable biomedical material.

As the outer diameter of the porous sleeve matches the inner diameter of the syringe barrel to form a cylindrical insert, this porous sleeve functions as a thin liner. The rigid syringe container provides a structural housing for the flowable implant material while the porous sleeve provides a pathway for steriliant gas penetration.

In this embodiment, there is also a piston 21 associated with the syringe container that has been adapted with a thin shaft (not shown) so that it may be used as a means of sealing the proximal end of the container and a means of dispensing the flowable biomedical material from the syringe container.

As shown, each end of the porous sleeve is exposed to the outer environment (i.e., it is not covered by the biomedical implant material). In this fashion, the porous sleeve can directly communicate with the steriliant gas to which the container is exposed.

The porous sleeve of this embodiment allows for rapid penetration of the sterilizing gas along the length of the sleeve, and therefore along the length of the syringe, thereby effectively reducing the maximum gas permeation distance of the device to one-half the inner diameter of the porous sleeve.

Figure 2:
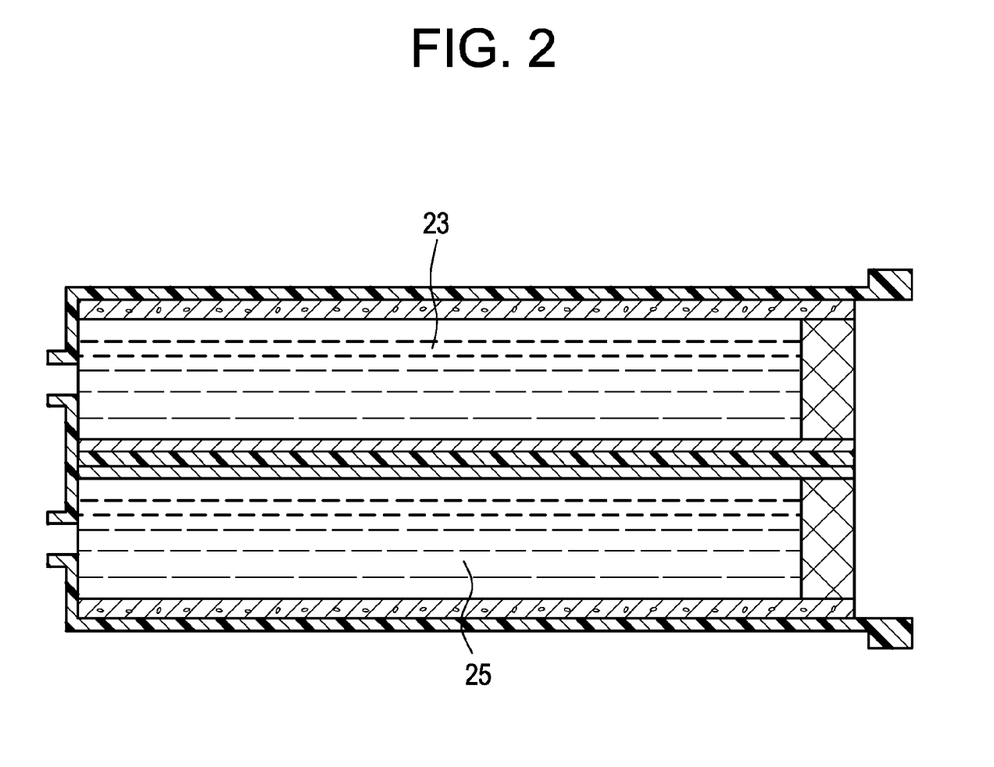
FIG. 2 is a longitudinal cross-section of a dual bore embodiment of the present invention having dual porous sleeves.

Now referring to FIG. 2, in a second embodiment of the present invention, there is provided a gas impervious container comprising two longitudinal bores having the associated openings, sleeves and pistons of the single bore embodiment shown in FIG. 1.

This device functions essentially the same way as the device of FIG. 1, except that it can hold a first material 23 in the first bore and a second different material 25 in the second bore. This embodiment is advantageous for the sterilization and dispensing of two curable materials that mix to form a biomedical implant material, such as silicone.

Figure 3:
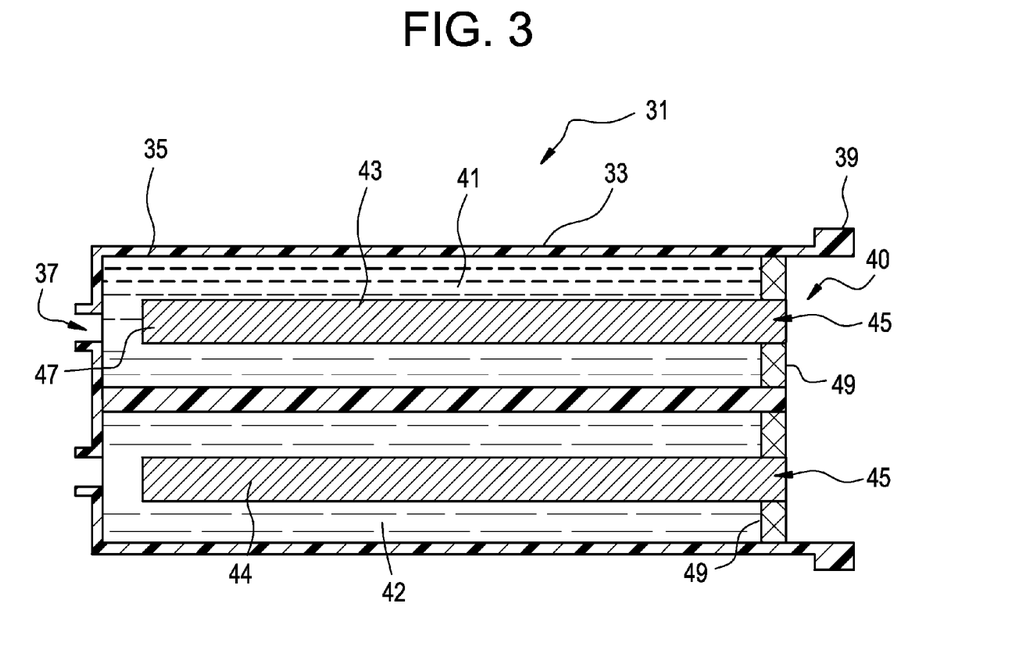
FIG. 3 is a longitudinal cross-section of a dual bore embodiment of the present invention having dual porous rods.

Now referring to FIG. 3, in a third embodiment of the present invention, there is provided a medical device 31 comprising:
   a) a gas-impervious container 33 having a bore defining a longitudinal axis, a distal end 35 having a distal opening 37, and a proximal end 39 having a proximal opening 40,
   b) a flowable biomedical material 41 contained within the bore of the container, and
   c) a gas-permeable porous rod 43 contained within the bore of the container and longitudinally disposed along the longitudinal axis of the container, the rod having a first end 45 and a second end 47,
wherein the rod contacts the flowable biomedical material.

In the third embodiment of the present invention, there is provided a syringe having a porous rod axially disposed within a bored syringe container. The porous rod may run the full length of the syringe and can have a diameter of about one-third of the diameter of the bore. The porous insert rod can be solid and may have any number of geometries, such as a cylinder, a square, a hollow tube, or a toroid. The rigid syringe provides a structural housing for the flowable implant material while the porous rod insert in either its hollow or solid configuration provides a pathway for steriliant gas penetration.

In this embodiment, there is also a piston 49 associated with the syringe container that has been adapted with a thin shaft (not shown) so that it may be used as a means of sealing the proximal end of the container and a means of dispensing the flowable biomedical material from the syringe container.

The porous rod allows for rapid penetration of the sterilizing gas along the length of the sleeve, and therefore along the length of the syringe, thereby effectively reducing the maximum gas permeation distance of the device to about one-third of the diameter of the syringe barrel.

This embodiment of FIG. 3 is a two-bore type embodiment similar to FIG. 2, and so contains a second flowable biomedical material 42 and a second gas-permeable porous rod 44.

Figure 4:
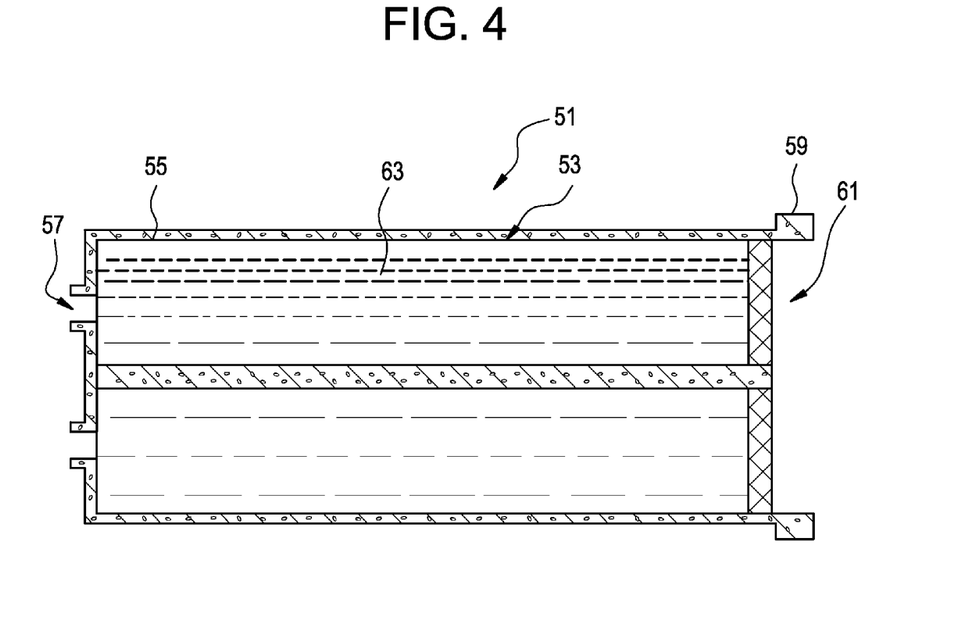
FIG. 4 is a longitudinal cross-section of a dual bore embodiment of the present invention having a porous container.

Now referring to FIG. 4, in a fourth embodiment of the present invention, there is provided a medical device 51 comprising:
a) a gas-permeable, liquid impermeable container 53 having a bore defining a longitudinal axis, a distal end 55 having a distal opening 57, and a proximal end 59 having a proximal opening 61,
b) a flowable biomedical material 63 contained within the bore of the container.

In a fourth embodiment of the present invention, there is provided a syringe that is substantially constructed of a porous material. The porous material must have a strength that is sufficient to handle pressure generated during the dispensing process. The porous syringe allows for rapid radial penetration of the gaseous sterilant through the barrel of the syringe and into the flowable implant material, thereby effectively reducing the maximum gas permeation distance to one-half the inner diameter of the syringe barrel.

In a fifth embodiment of the present invention, there is provided a cartridge and cartridge insert combination that are sterilized independently and then assembled at the point of use. The cartridge is similar in design to a conventional cartridge but has been modified to accept and puncture an insert containing sterile product. The cartridge insert is constructed of a thin-membrane like porous material to allow for rapid gas penetration. The thin-membrane like porous material effectively reduces the gas permeation distance to half the inner diameter of the syringe barrel.

Figure 5:
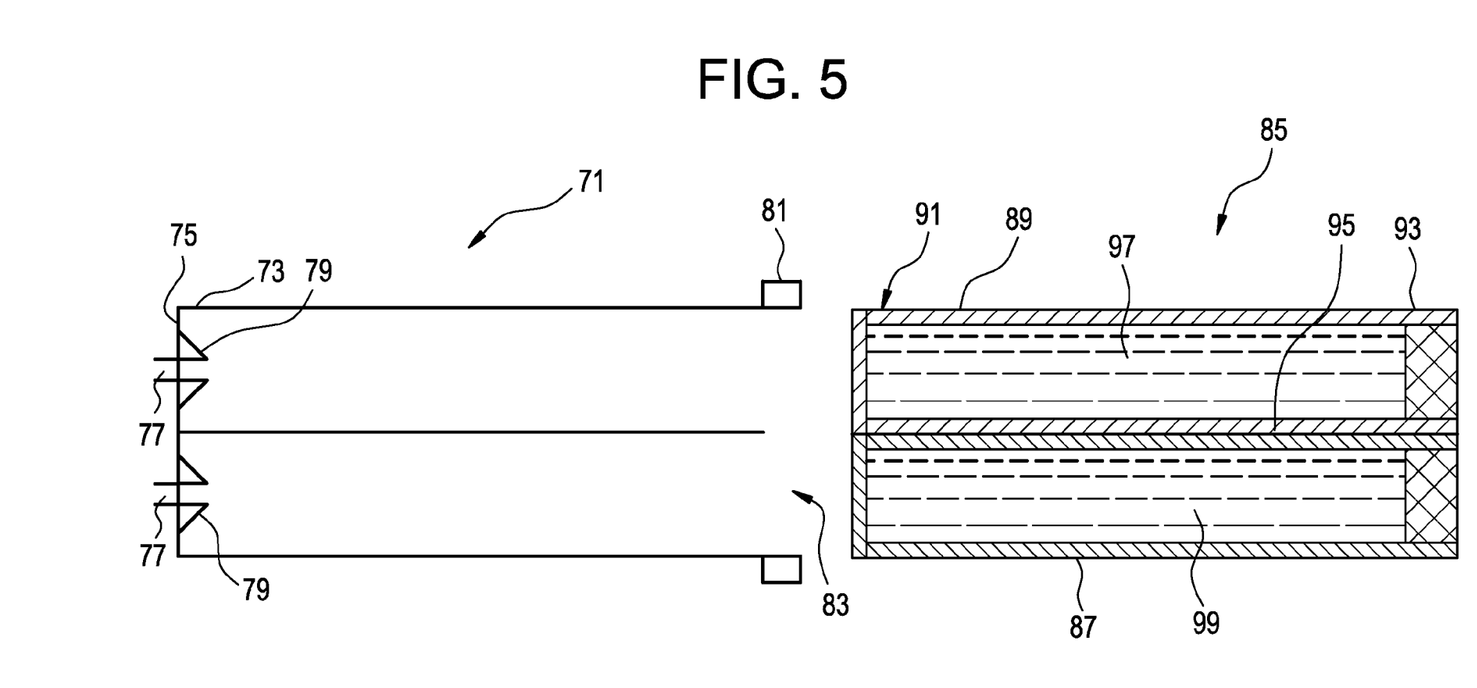
FIG. 5 is a longitudinal cross-section of a kit of the present invention having a porous cartridge and a container.

Now referring to FIG. 5, there is provided a kit comprising:
a) a cartridge 71 having a first bore defining a longitudinal axis, a distal end 73 having a distal endwall 75, distal openings 77 and activation means 79, and a proximal end 81 having a proximal opening 83,
b) a cartridge insert 85 comprising:
i) a gas-permeable, liquid impermeable container 87 having an outer wall 89, a distal end 91, a proximal end 93, and a central wall 95 defining upper and lower longitudinal bores therein,
ii) a first flowable biomedical material 97 contained within the upper bore of the container, and
iii) a second flowable biomedical material 99 contained within the lower bore of the container.

The activation means is a means for puncturing the distal end of the insert, so that flowable material may flow out of the distal end of the insert. In this particular FIG. 5, the activation means are spikes that puncture the distal end of the insert. However, in other embodiments, the activation means may be valves or stopcocks.

In use, both the cartridge and the insert are separately sterilized, and then the insert in inserted into the cartridge. As the distal end of the insert nears the distal end of the cartridge, the distal end of the insert is punctured by the proximally facing spikes, thereby causing flowable material contained in the insert to flow out of the distal end of the cartridge and through distal openings 77.

Figure 6:
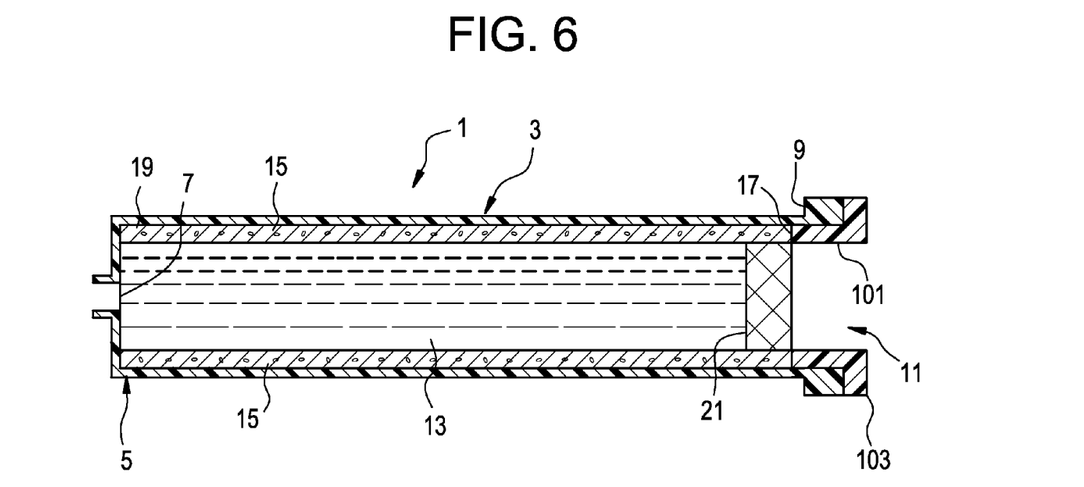
FIG. 6 discloses a cross-section of a device of the present invention including a gasket seal.

If sealing becomes an issue, then a coating or a gasket seal may be used to prevent seepage. Now referring to FIG. 6, there is provided a gasket seal with a locking ring, wherein the seal prevents liquids from penetrating through the porous sleeve when under pressure that occurs during fluid dispensing. Now referring to FIG. 6, in another embodiment of the present invention, there is provided a medical device 1 comprising:
a) a gas-impervious container 3 having a bore defining a longitudinal axis, a distal end 5 having a distal opening 7, and a proximal end 9 having a proximal opening 11,
b) a flowable biomedical material 13 contained within the bore of the container,
c) a gas-permeable porous sleeve 15 contained within the bore of the container and longitudinally disposed along the longitudinal axis of the container, the sleeve having a first end 17 and a second end 19, and
d) a gasket seal 101 having a locking ring 103, wherein the gasket seal contacts the first end of the porous sleeve,
wherein the sleeve contacts the flowable biomedical material.

Example I

The following example provides test sterilization data of one embodiment of the present invention.

Baseline testing of an open tray containing an inoculated wire with a known microbial population and covered with bulk Sinux™ gel indicates that at 7 hours of Ethylene Oxide gas exposure, complete kill is achieved when the gel thickness is about 5 mm. In contrast, sterilization testing using conventional technology indicates that after 24 hours of gas exposure, the affect on the microbial population is minimal. In this case the spore log reduction, or the number of logarithms that the microbial population is reduced during the sterilization cycle (SLR), is small (SLR=1.0).

Test data with a mock-up of the third embodiment of the present invention resulted in a significantly greater SLR than that of conventional technology, and at much shorter exposure times. In particular, the second embodiment provided an SLR of about 3.9 at an exposure time of only 7 hours. These preliminary data tend to show that a reduction in the maximum gas permeation distance of the system allows for a quicker and more effective gas penetration and has shown that total kill can be achieved when gas permeation distance is radially 5 mm or less.

Example II

The following example provides test sterilization data for different embodiments of the present invention. In this example, air bubbles were minimized during the filling of the porous sleeves by using prefilled cartridges to dispense the flowable biomedical material into the porous sleeve or rod. An upside-down, bottom fill technique was used, with the flowable material dispensing tip facing up, and the porous sleeve or rod on top of it, dispensing the flowable material against gravity.

The sleeve was sterilized in three configurations at a gas exposure time of 7 hours. One as a standalone porous sleeve, another with a porous sleeve inserted into the cartridge and a third with a porous rod inserted into the center of a cartridge. The results of the testing were as follows:

| | Results | | |
|---|---|---|---|
| Config | Description | Sample 1 SLR | Sample 2 SLR |
| A | Third Embodiment 3 - Cartridge with Porous Central Rod | 4.91 | 4.83 |
| B | Second Embodiment 2 - Cartridge with Porous Sleeve | 1.61 | 3.11 |

-continued

| Config | Description | Sample 1 SLR | Sample 2 SLR |
|---|---|---|---|
| C | Fifth Embodiment - Standalone Porous Sleeve | 6.68 | 6.68 |
|  | Conventional Technology (previous test t = 24 hours) | ~1.0 | |

Total kill was achieved on the standalone porous sleeves. It may be concluded that configurations A and C were highly effective in reducing spore population.

It was further found that the flowable material of Configurations B and C weeped through the porous sleeves prior to the run. The samples had been prepared on the day prior to the run. The less promising result achieved by Configuration B may be due to the fact that pore occlusion and weeping of the flowable material through the porous sleeve occurred, creating direct contact of flowable material with the cartridge wall, and thereby reducing the exposed surface area of the porous sleeve.

We claim:

1. A method of sterilizing a biomedical material, comprising the steps of:

a) providing a gas-impervious container having an open end and flowable biomedical material therein and a gas-permeable porous insert, and b) exposing the open end of the container to a gaseous sterilant, c) using the biomedical implant material in a biomedical procedure, wherein the container is substantially cylindrical and has a longitudinal axis, wherein the insert is disposed along the longitudinal axis of the substantially cylindrical container, and wherein the insert contacts the flowable biomedical material along the longitudinal axis, wherein the insert extends through the container, and wherein the exposure of the open end of the container to the gaseous sterilant is sufficient to sterilize the flowable biomedical material contained therein.

2. The method of claim 1 wherein a first end of the insert is exposed to the sterilant.

* * * * *